(12) United States Patent
Gehlsen

(10) Patent No.: US 6,270,781 B1
(45) Date of Patent: Aug. 7, 2001

(54) METHOD AND COMPOSITIONS FOR TOPICAL TREATMENT OF DAMAGED TISSUE USING REACTIVE OXYGEN METABOLITE PRODUCTION OR RELEASE INHIBITORS

(75) Inventor: Kurt R. Gehlsen, Encinitas, CA (US)

(73) Assignee: Maxim Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/227,801

(22) Filed: Jan. 8, 1999

(51) Int. Cl.[7] .................................................. A61K 7/021
(52) U.S. Cl. ........................ 424/401; 424/64; 424/701; 514/725
(58) Field of Search ........................ 424/401, 64, 70.1; 514/725

(56) References Cited

U.S. PATENT DOCUMENTS

| | | |
|---|---|---|
| 4,307,076 | 12/1981 | Harvey et al. . |
| 4,573,996 | 3/1986 | Kwiatek et al. . |
| 4,597,961 | 7/1986 | Etscom . |
| 4,839,174 | 6/1989 | Baker et al. . |
| 4,857,328 | 8/1989 | Trenzeluk . |
| 4,908,213 | 3/1990 | Govil et al. . |
| 4,943,435 | 7/1990 | Baker et al. . |
| 5,116,620 | 5/1992 | Chvapil et al. . |
| 5,122,127 | 6/1992 | Stanley . |
| 5,160,731 | 11/1992 | Sabetelli et al. . |
| 5,288,497 | 2/1994 | Stanley et al. . |
| 5,294,440 | 3/1994 | Jack et al. . |
| 5,328,454 | 7/1994 | Sibalis . |
| 5,336,168 | 8/1994 | Sibalis . |
| 5,474,527 | 12/1995 | Bettinger . |
| 5,558,914 | 9/1996 | Cohen et al. . |
| 5,676,969 | 10/1997 | Wick et al. . |
| 5,679,337 | 10/1997 | Jack et al. . |
| 5,716,610 | 2/1998 | Jack et al. . |
| 5,804,203 | 9/1998 | Hahn et al. . |

FOREIGN PATENT DOCUMENTS

| | | |
|---|---|---|
| 93/21904 | 11/1993 | (WO) . |
| 95/23601 | 9/1995 | (WO) . |
| WO 97/42968 | * 11/1997 | (WO) . |
| 97/472968 | 11/1997 | (WO) . |

OTHER PUBLICATIONS

Brune, M. et al. (1996) NK cell–mediated killing of AML blasts: role of histamine, monocytes and reactive oxygen metabolites. Eur. J. Haematol. 57:312–319.

Babior, et al., The Journal of Clinical Investigaton, 52(3): 714–744 (1973) "Biological Defense Mechanisms: The production by leukocytes of superoxide, a potential bacterial agent".

Imamura, et al., Pathology International, 47(1): 16–24 (1997), "Involvement of tumor necrosis factorα, interleukin–1β, interleukin–8, and interleukin–1 receptor antagonist in acute lung injury caused by local Scwartzman reaction".

Paul and Sbarra, Biochima Et Biophysica Acta, 156: 168–178 (1968) "The Role of the Phagocyte in Host–Parasite Interactions".

Martindale—The Extra Pharmacopoeia (Pharmaceutical Press,London 1993) and Martin (ed.), Remington's Pharmaceutical Sciences.

CFTA Cosmetic Ingredient Handbook, $2^{nd}$ Edition, eds. John A. Wenninger and G.N. McEwen, Jr. (CTFA, 1992).

Anthony, L.L. (ed.), "A Formulary of Cosmetic Preparations (vol. Two)—Creams, Lotions and Milks, " Micelle Press (England, N.J., 1993).

http:/www.shaperite.com/prod/pc24.html, "Smooth–Rite Pain Cream" (Oct. 16, 1998).

http:/www.cyberspike.com/chiro/remedies/hist15.html, "Histamine", BioPharma—All Natural Homeopathic Remedies (Dec. 21, 1998).

21 CFR Ch. 1 §310.545 (Apr. 1, 1998 Edition).

* cited by examiner

*Primary Examiner*—Michael A. Williamson
(74) *Attorney, Agent, or Firm*—Knobbe, Martens, Olson & Bear, LLP

(57) ABSTRACT

The present invention relates to compositions and methods for treating cell damage caused by reactive oxygen species in relation to a variety of skin disorders. More specifically, the present invention relates to the treatment skin disorders through the topical delivery of reactive oxygen metabolite production or release inhibiting compounds.

9 Claims, No Drawings

METHOD AND COMPOSITIONS FOR TOPICAL TREATMENT OF DAMAGED TISSUE USING REACTIVE OXYGEN METABOLITE PRODUCTION OR RELEASE INHIBITORS

BACKGROUND OF THE INVENTION

The present invention relates to compositions and methods for treating cell damage caused by reactive oxygen species in relation to a variety of skin or mucosal membrane disorders. More specifically, the present invention relates to the treatment of skin and mucosal membrane disorders through the topical delivery of compounds that inhibit the production or release of reactive oxygen metabolites.

Reactive oxygen metabolites (ROMs) are often produced by the incomplete reduction of oxygen. The complete reduction of one molecule of $O_2$ to water is a four-electron process. Oxidative metabolism continually generates partially reduced species of oxygen, which are far more reactive, and hence more toxic than $O_2$ itself. A one-electron reduction of $O_2$ yields superoxide ion ($O_2^-$); reduction by an additional electron yields hydrogen peroxide ($H_2O_2$), and reduction by a third electron yields a hydroxyl radical (OH.), and a hydroxide ion. Nitrous oxide (NO), is another interesting reactive oxygen metabolite, produced through an alternative pathway. Hydroxyl radicals in particular are extremely reactive and represent the most active mutagen derived from ionizing radiation. All of these species are generated and must be converted to less reactive species if the organism is to survive.

Particular cells of the immune system have harnessed the toxic effects of ROMs as an effector mechanism. Professional phagocytes, polymorphonuclear leukocytes (neutrophils, PMN), monocytes, macrophages, and eosinophils function to protect the host in which they reside from infection by seeking out and destroying invading microbes. These phagocytic cells possess a membrane-bound enzyme system that can be activated to produce toxic oxygen radicals in response to a wide variety of stimuli.

The "increased respiration of phagocytosis" (the respiratory burst) was reported and thought to be a result of increased mitochondrial activity providing additional energy for the processes of phagocytosis. It was later shown that a non-mitochondrial enzymatic system produced the increased levels of oxygen metabolites since the respiratory burst continued even in the presence of mitochondrial inhibitors such as cyanide and antimycin A. In 1968, Paul and Sbarra showed clearly that stimulated phagocytes produced hydrogen peroxide and in 1973 Babior and co-workers established that superoxide was a major product of the oxidase. (Paul and Sbarra, *Biochim Biophys Acta* 156 (1): 168–78 (1968); Babior, et al., *J Clin Invest* 52(3): 741–4 (1973). It is now generally accepted that the enzyme is membrane bound, exhibits a preference for NADPH ($K_m$=45 µM) over NADH ($K_m$=450 µM), and converts oxygen to its one electron-reduced product, superoxide.

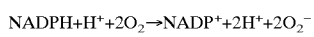

The hydrogen peroxide arises from subsequent dismutation of the superoxide.

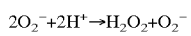

The enzyme activity is almost undetectable in resting (unstimulated) phagocytes, but increases dramatically upon stimulation. Patients with the rare genetic disorder chronic granulomatous disease (CGD), have a severe predisposition to chronic recurrent infection. The neutrophils from these patients phagocytose normally but the respiratory burst is absent and NADPH oxidase activity (and radical production) is undetectable, indicating that the oxidase and its product, the reactive oxygen metabolites, have an important bactericidal function.

Neutrophils and macrophages produce oxidizing agents to break through the protective coats or other factors that protect phagocytosed bacteria. The large quantities of superoxide, hydrogen peroxide, and hydroxyl ions are all lethal to most bacteria, even when found in very small quantities.

While there are beneficial effects of these oxygen metabolites, it is clear that inappropriate production of oxygen metabolites can result in severely deleterious effects. A number of these deleterious effects manifest themselves in the dermal tissues and mucosal membranes of the host. For example, a variety of skin disorders including herpes simplex infections, and chemical and heat induced skin lesions can be exacerbated by unwanted concentrations of reactive oxygen metabolites. Effective compositions and methods to reduce and minimize the production and release of ROMs in patients suffering from a variety of disparate disorders would be a great boon to medicine and serve to reduce and eliminate a substantial amount of human suffering.

Topically administered salves, balms and other such medicaments are well known in the art. The application of mud or plant extracts such as aloe vera are just two examples of such medicaments. For a discussion of aloe vera, see U.S. Pat. No. 4,857,328, which is hereby incorporated by reference. The use of two different histamine derivatives as topically administered skin medicaments has also been discussed previously. The first may be found in a series of U.S. Patents to Jack et al., which disclose the use of a pharmaceutical composition of water, water soluble vinyl polymer gel, an amine alcohol dispersant and 1H-imidazole-4-ethanamine phosphate to treat certain skin disorders. See U.S. Pat. Nos. 5,294,440; 5,679,337; and 5,716,610. The second is found in U.S. Pat. No. 5,792,784, that discloses a pseudo-dipeptide product obtained by coupling histamine or a methyl-substituted histamine and an amino acid.

SUMMARY OF THE INVENTION

The present invention is directed to methods and compositions for reducing enzymatically produced ROM-mediated damage to a subject's skin or mucosal membranes by the topical application of ROM production and release inhibiting compositions. One embodiment of the present invention is a method for inhibiting and reducing enzymatically produced ROM-mediated oxidative damage to a subject's skin or mucosal membranes comprising the step of topically delivering an effective dose of a ROM production and release inhibitory compound in a pharmaceutically acceptable carrier to a subject suffering from ROM-mediated oxidative damage to said subject's skin or mucosal membranes.

In one aspect of this embodiment, the ROM-mediated oxidative damage to said subject's skin or mucosal membranes is a viral disease selected from the group consisting of herpes labialis, herpes genitalis, herpes zoster, and varicella zoster. In another aspect, the ROM-mediated oxidative damage to said subject's skin or mucosal membranes results from an injury selected from the group consisting of photodermatitis, thermal burns, lacerations, and cosmetic surgery.

In another embodiment of the present invention the ROM production and release inhibitory compound is selected from the group consisting of histamine, histamine dihydrochloride, histamine diphosphate, other histamine salts, esters, prodrugs, $H_2$ receptor agonists, serotonin, and 5HT agonists. In another embodiment, the ROM production and release inhibitory compound is a compound that promotes the release of endogenous histamine stores. In an aspect of this embodiment, compounds that promote the release of endogenous histamine stores are selected from the group consisting of IL-3, retinoic acid, 9-cis-retinoic acid, all-trans-retinoic acid, and allergens.

Another embodiment of the present invention contemplates a composition comprising an effective dose of a compound that inhibits the production or release of enzymatically produced ROMs in a pharmaceutically acceptable carrier adapted for topical delivery. In one aspect of this embodiment, the compound is selected from the group consisting of histamine, histamine dihydrochloride, histamine diphosphate, other histamine salts, esters, prodrugs, $H_2$ receptor agonists, serotonin, and 5HT agonists. In another aspect, the compound is a compound that promotes the release of endogenous histamine stores. In still another aspect, the compound that promotes the release of endogenous histamine stores is selected from the group consisting of IL-3, retinoic acid, 9-cis-retinoic acid, all-trans-retinoic acid, and allergens. In still another aspect of this embodiment, the pharmaceutically acceptable carrier is a cosmetic product, such as a sunscreen, a toothpaste, a soap, a wound dressing, a spray, a mouthwash, or a transdermal patch.

In still another embodiment of the present invention, a method for making a composition for topically delivering histamine comprising the steps of providing a pharmaceutically acceptable carrier and histamine in a concentration effective to treat a ROM mediated damage to the skin or mucosa caused by a disorder of the skin or mucosa selected from the group consisting of herpes labialis, herpes genitalis, herpes zoster, varicella zoster, photodermatitis, thermal burns, cosmetic surgery and periodontal disease, and forming a composition containing the pharmaceutically acceptable carrier and a compound that inhibits the production and release of enzymatically produced ROMs.

In yet another embodiment of the present invention, the making of the compositions involves selecting the compound from the group consisting of histamine, histamine dihydrochloride, histamine diphosphate, other histamine salts, esters, prodrugs, $H_2$ receptor agonists, serotonin, and 5HT agonists. In another embodiment, the claimed methods of the present invention are within ROM production and release inhibitory compound is a compound that promotes the release of endogenous histamine stores.

The compositions of the present invention can be found in a variety of cosmetic illusion. For example, the composition can be a lipstick, a shampoo, a carrier, a mouthwash, or a transdermal patch.

DETAILED DESCRIPTION OF PREFERRED EMBODIMENTS OF THE INVENTION

The present invention relates to compositions and methods for the reduction of reactive oxygen metabolite mediated damage in the treatment of skin and mucosal membrane disorders caused by or aggravated by reactive oxygen metabolites. The compositions and methods of the present invention are useful, for example, for treating certain disorders caused by various disease etiologies, and lesions of the skin, such as burns.

When skin injury occurs, whether caused by bacteria, trauma, chemicals, heat, or any other phenomenon, multiple substances that cause dramatic secondary changes in the tissues are released. These secondary changes are called inflammation. Secondary changes, or inflammation can result from a variety of skin injuries including but not limited to: viral diseases that affect the skin including, herpesvirus infections, such as cold sores, genital herpes, shingles, chickenpox; aphthous stomatitis, oral mucositis; and lesions or injury to the skin such as photodermatitis (sunburn, specifically second degree sunburn), thermal burns and pressure sores (decubitus ulcers). Inflammation is characterized by vasodilation of the local blood vessels, creating excess local blood flow, increased permeability of the capillaries with leakage of large quantities of fluid into the interstitial spaces, and other effects.

Soon after the onset of inflammation, neutrophils, macrophages, and other cells invade the inflamed area. These cells set about to rid the tissue of infectious or toxic agents. One method these cells use to defend the body from harmful foreign substances includes the production and release of reactive oxygen metabolites.

A variety of reactive oxygen metabolites are produced in the monovalent pathway of oxygen reduction. These ROMs are enzymatically produced by phagocytes such as monocytes and polymorphonuclear neutrophils (PMNs) and frequently released in a respiratory burst. Hydrogen peroxide and other ROMs play an important role in a host's immunological defenses. Nevertheless, ROMs produced in excessive amounts or at inappropriate times or locations, act to damage a host's cells and tissues, and thus can be detrimental to the host.

The effects of ROM production are many faceted. ROMs are known to cause apoptosis in NK cells. ROMs are also known to cause anergy and apoptosis in T-cells. The mechanisms by which ROMs cause these effects are not fully understood. Nevertheless, some commentators believe that ROMs cause cell death by disrupting cellular membranes and by changing the pH of cellular pathways critical for cell survival.

Additionally, phagocytes that undergo a respiratory burst, and produce and release large quantities of ROMs also produce and release secondary cytokines such as tumor necrosis factor-alpha (TNF-α) and interleukin-1 (IL-1). An example of secondary cytokine mediated cell damage is found in the Shwartzman Reaction, where neutrophil mediated cell damage is thought to be activated by TNF and IL-1. Imamura S, et al., "Involvement of tumor necrosis factor-alpha, interleukin-1 beta, interleukin-8, and interleukin-1 receptor antagonist in acute lung injury caused by local Shwartzman reaction" Pathol Int. 47(1): 16–24 (1997). This ROM and cytokine release augments the cell damage inflicted by a variety of sources as these potent chemical compounds are disseminated throughout the body. Although released as a defensive measure by the cells of the immune system, the ROMs result in ROM-mediated cell damage and the secondary cytokines cause a rapid deterioration of the patient, resulting often in death.

It is one of the surprising discoveries of the present invention that compounds that reduce or inhibit the amount of ROMs and secondary cytokines produced or released by sources within a subject can facilitate the treatment and recovery of individuals suffering from a variety of skin and mucosal conditions. Some of the conditions contemplated as treatable under the present invention result from a disparate number of etiological causes. Nevertheless, they share a common feature in that their pathological conditions are either caused or exacerbated by enzymatically produced, ROM-mediated oxidative damage, caused by inappropriate and harmful concentrations of ROMs. Thus, the administration of compounds that inhibit the production or release of ROMs, or scavenge ROMs, alone or in combination with other beneficial compounds, provides an effective treatment for a variety of skin and mucosal conditions.

Accordingly, the present invention contemplates utility in treating herpes infections, including treatment of herpes labialis and herpes genetalis alone or in conjunction with other therapeutic compounds, treatment of herpes labialis using a cosmetic, treatment of pharyngotonsillitis, treatment of keratoconjunctivitis, treatment of varicella-zoster virus (chicken pox) infections, and treatment of herpes zoster (shingles) lesions. The compositions and methods of the present invention also contemplate utility in the treatment of skin disorders such as psoriasis, eczema, acne, canker sores, warts and other skin and mucosal conditions or disease states.

The compounds and methods of the present invention also contemplate utility in the treatment and reduction of photodermatitis (second degree sunburn), chemical burns, and the treatment of thermal burn injuries. The present invention also has utility in promoting incision healing generally, as well as facilitating the healing process in various cosmetic surgical procedures such as chemical peels, laser treatments dermabrasion and other techniques like face-lifts, eyelid surgery, and the like. The compounds and methods of the present invention also have utility in treating periodontal disease and for use following periodontal surgery to facilitate healing. The present invention further contemplates utility in the treatment of mucus membranes in the mouth for mucositis induced by chemotherapy or radiotherapy.

Formulations of the Present Invention

The administration of the ROM production or release inhibiting or scavenging compounds of the present invention is contemplated to be via a topical route. To facilitate this route of administration, a variety of formulations for the topical application of the compounds of the present invention are contemplated. The formulations of the present invention facilitate the topical administration of compounds that inhibit the production or release of reactive oxygen metabolites or scavenge these compounds once released. The topical formulations contemplated here comprise a topical vehicle suitable for the administration of an effective amount of the ROM inhibiting and/or scavenging compounds of the present invention.

The present invention contemplates using various histamine or histamine-related compounds to achieve a beneficial reduction in the concentration of enzymatically produced ROM production and release. The present invention is also directed at inhibition ROM production and release. The term "histamine" as used herein incorporates a variety of histamine and histamine related compounds. For example, histamine, the dihydrochloride salt form of histamine (histamine dihydrochloride), histamine diphosphate, other histamine salts, esters, or prodrugs, and $H_2$ receptor agonists are to be included. The topical administration of compounds that induce the release of endogenous histamine from a patient's own tissue stores is also included within the scope of the present invention. Such compounds include IL-3 retinoic acid, other retinoids such as 9-cis-retinoic acid and all-trans-retinoic acid, and allergens. Other ROM production and release inhibitory compounds such as NADPH oxidase inhibitors like diphenlyeneiodonium are also within the scope of the present invention. The topical administration of serotonin and 5HT agonists in the present invention is also contemplated.

The topical formulations contain the ROM inhibitory or scavenging compounds of the present invention in a concentration effective to prevent or reduce ROM mediated damage. When the topical formulation contains an ROM inhibitory compound, it preferably contains this component in a total concentration of about 0.0001 to about 0.5 percent by weight of formulation, more preferably about 0.001 to about 0.01 percent by weight of formulation, and most preferably about 0.002 to 0.05 percent by weight of formulation.

The compositions and methods of the present invention further contemplate topically administrating a variety of ROM scavengers in conjunction with the ROM production and release inhibiting compounds described above. Known scavengers of ROMs include the enzymes catalase, superoxide dismutase (SOD), glutathione peroxidase and ascorbate peroxidase. Additionally, vitamins A, E, and C are known to have scavenger activity. Minerals such as selenium and manganese can also be efficacious in combating ROM-mediated damage. It is intended that the present invention include the topical administration of the compounds listed and those compounds with similar ROM inhibitor activity.

Compounds that scavenge ROMs can be administered in a total concentration of about 0.0001 to about 0.5 percent by weight of formulation, more preferably about 0.001 to about 0.01 percent by weight of formulation, and most preferably about 0.002 to 0.05 percent by weight of formulation. Formulations containing ROM scavengers are topically applied from 1 to 10 times per day. In each case, the dose and times of application depend on the activity of the administered compound. The foregoing doses are appropriate for the compounds listed above. Appropriate doses for any particular host can be readily determined by empirical techniques well known to those of ordinary skill in the art.

Nonenzymatic ROM scavengers can be topically administered in amounts empirically determined by one of ordinary skill in the art. For example, vitamins A and E can be topically administered in doses from about 1 to 5000 IU per dose. Vitamin C can be topically administered in doses from 1 $\mu$g to 10 gm per dose. Minerals such as selenium and manganese can be topically administered in amounts from about 1 picogram to 1 milligram per dose. These compounds can also be topically administered as a protective or preventive treatment for ROM mediated disease states.

The preferred concentration ranges expressed above are generally effective to inhibit the production of or scavenge ROMs already present in the treated area of a subject. Higher concentrations may also be successfully used. Moreover, routine clinical assessments can be used to optimize the concentration of the present invention's compounds. For example, the concentration of histamine can be adjusted to accommodate a skin injury based upon the total area to be treated. Concentrations can also vary based upon the vehicle used as the formulation. A lotion, which is designed to blend into the skin leaving no visible trace might contain a lower concentration of histamine when compared to a cream that is formulated to dry on the skin of the treated subject.

The concentration of the ROM inhibiting or scavenging compounds of the present invention can vary in accordance with the other ingredients used in the topical formulation. For example, histamine concentrations can be decreased when compounds that reduce skin irritation are included, such as strontium, aloe vera, chamomile, abisabolol, cola nitida extract, green tea extract, tea tree oil, licorice extract, allantoin, urea, caffeine or other xanthines, and glycyrrhizic acid and its derivatives. These compounds can also be used in the formulation of the present invention in conjunction with the ROM inhibiting or scavenging compounds discussed above. These compounds can be added to the compositions singularly or in combination with each other. For the use of strontium as a skin anti-irritant see U.S. Pat. No. 5,804,203, hereby incorporated by reference.

In addition, inclusion of various antiviral agents in the topical compositions of the present invention are contemplated. Examples of these agents include 9-(2-Hydroxyethoxymethyl)guanine, ZOVIRAX (GlaxoWellcome), idoxuridine, trifluorothymidine, bromovinyldeoxyuridine, ribavirin, amantadine, rimantadine, nevirapine (NVP), zidovudine (ZDV), 3'-azido-3'deoxythymidine (AZT), 2',3'-dideoxyinosine (ddI), 2',3'-dideoxycytidine (ddC), 2',3'-didehydro-2'3'-dideoxythymidine (d4T), and (−)-beta-L-2',3'-dideoxy-3'-thiacytidine (3TC) and the like.

Further, the inclusion of substances such as analgesics are contemplated for inclusion in the topical compositions of the present invention. Also, compounds that result in the stimulation of a host's immune system such as cytokines, (e.g., IL-1, IL-2, IL-12, IL-15, IFN-$\alpha$, IFN-$\beta$, IFN-$\gamma$ and the like) are contemplated for inclusion in the topical compositions of the present invention.

The antiviral compounds, the analgesics, and the immuno-stimulatory compositions can be added singularly to the compositions of the present invention, or in combination with each other.

Suitable topical vehicles and components for use with the formulations of the present invention are well known in the art. Such vehicles include water; organic solvents such as alcohols (such as ethanol); glycols (such as propylene glycol); aliphatic alcohols (such as lanolin); mixtures of water and organic solvents and mixtures of organic solvents such as alcohol and glycerin; lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile); hydrocarbon-based materials such as microsponges and polymer matrices; stabilizing and suspending agents; emulsifying agents; and other vehicle components that are suitable for administration to the skin, as well as mixtures of these components and those otherwise known in the art. The vehicle can further include components adapted to improve the stability or effectiveness of the applied formulation, such as preservatives, antioxidants, skin penetration enhancers and sustained release materials. Examples of such components are described in the following reference works hereby incorporated by reference: *Martindale—The Extra Pharmacopoeia (Pharmaceutical Press, London* 1993) *and Martin* (ed.), *Remington's Pharmaceutical Sciences.*

The choice of a suitable vehicle will depend on the particular physical form and mode of delivery that the formulation is to achieve. Examples of suitable forms include liquids (e.g., eye drops, gargles and mouthwashes); solids and semisolids such as gels, foams, pastes (such as topically applied pastes as well as toothpaste compositions), creams, ointments, "sticks" (such as lipsticks or underarm deodorant sticks), powders and the like; formulations containing microcapsules prepared, for example, by coacervation techniques, or by interfacial polymerization, for example hydroxymethylcellulose or gelatin-microcapsules, respectively, or in colloidal drug delivery systems, for example, liposomes, albumin microspheres, microemulsions, nanoparticles, and nanocapsules, or in macroemulsions; rectal or vaginal suppositories, creams, foams, gels or other ointments; and other forms. An example of toothpastes can be found in U.S. Pat. No. 4,307,076, which discusses toothpaste compositions and is hereby incorporated by reference.

The topical formulations of the present invention can be prepared in a variety of physical forms. For example, solids, pastes, creams, lotions, gels, and aqueous liquids are all contemplated by the present invention. A difference between these forms is their physical appearance and viscosity, which can be governed by the presence and amount of emulsifiers and viscosity adjusters present in the formulation. Particular topical formulations can often be prepared in a variety of these forms. Solids are generally firm and non-pourable and commonly are formulated as bars or sticks, or in particulate form; solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams may also contain solvents, emulsifiers, moisturizers, emollients, fragrances, dyes/colorants, preservatives and other active ingredients that increase or enhance the efficacy of the final product. Liquids are thinner than creams, lotions, or gels and often do not contain emulsifiers. Liquid topical products often contain solvents, emulsifiers, moisturizers, emollients, fragrances, dyes/colorants, preservatives and other active ingredients that increase or enhance the efficacy of the final product.

Suitable emulsifiers for use in the formulations of the present invention include, but are not limited to ionic emulsifiers; behentirmonium methosulfate, cetearyl alcohol; non-ionic emulsifiers like polyoxyethylene oleyl ether, PEG-40 sterate, ceteareth-12, ceteareth-20, ceteareth-30, ceteareth alcohol, PEG-100 stearate, glyceryl stearate, or combinations or mixtures thereof.

Suitable viscosity adjusting agents for use in the formulations of the present invention include, but are not limited to protective colloids or non-ionic gums such as hydroxyethylcellulose, xanthan gum, magnesium aluminum silicate, silica, microcrystalline wax, beeswax, paraffin, and cetyl palmitate, or combinations or mixtures thereof.

Suitable solvents for use in the formulations of the present invention include, but are not limited to water, ethanol, butylene glycol, propylene glycol, isopropyl alcohol, isoprene glycol, and glycerin. In addition, combinations or mixtures of these solvents can be used in the formulations of the present invention.

Suitable surfactants for use in the formulations of the present invention include, but are not limited to nonionic, amphoteric, ionic and anionic surfactants. For example, dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate are contemplated for use with the formulations of the present invention. In addition, combinations or mixtures of these surfactants can be used in the formulations of the present invention.

Suitable preservatives for use in the formulations of the present invention include, but are not limited to antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. In addition, combinations or mixtures of these preservatives can be used in the formulations of the present invention.

Suitable moisturizers for use in the formulations of the present invention include, but are not limited to lactic acid and other hydroxy acids and their salts, glycerin, proplyene glycol, and butylene glycol. Suitable emollients include lanolin alcohol, lanolin, lanolin derivatives, cholesterol, petrolatum, isostearyl neopentanoate and mineral oils. In addition, combinations or mixtures of these moisturizers and emollients can be used in the formulations of the present invention.

Suitable active ingredients in addition to the ROM production and release inhibiting compounds for use in the formulations of the present invention include, but are not limited to alpha hydroxy acids, sunscreens, anti-acne drugs, vitamins and minerals, and various prescription and over-the-counter medications. An example of a sunscreen can be found in US. Pat. No. 5,160,731, hereby incorporated by reference. The present invention also contemplates the inclusion of multiple additional active ingredients such as those listed above.

Suitable fragrances and colors for use in the formulations of the present invention include, but are not limited to, FD&C Red No. 40 and FD&C Yellow No. 5. Other examples of fragrances and colors suitable for use in topical products are known in the art.

Other suitable additional ingredients that may be included in the formulation of the present invention include, but are not limited to, abrasives, absorbents, anti-caking agents, anti-foaming agents, anti-static agents, astringents (e.g., witch hazel, alcohol and herbal extracts such as chamomile extract), binders/excipients, buffering agents, chelating agents, film forming agents, conditioning agents, opacifying agents, pH adjusters and protectants. Examples of each of these ingredients in topical product formulations, can be found in publications by The Cosmetic, Toiletry, and Fragrance Association (CTFA). See, e.g., CTFA *Cosmetic Ingredient Handbook*, $2^{nd}$ edition, eds. John A. Wenninger and G. N. McEwen, Jr. (CTFA, 1992).

Also, a variety of product types, including particularly cosmetics, can be formulated in each of the forms described above (i.e., solids, creams, lotions, gels, and liquids). For example, cleansers (such as soaps), shampoos/conditioners, make-up products, and other facial, hand and body products can be formulated in any of the product forms described above: solids, creams, lotions, gels, or liquids. Common solid form products include cosmetics such as lipsticks, blushes, other makeup products, lozenges and suppositories. Common cream and lotion form products include moisturizing products, sunscreens, shampoos/conditioners and other hair care products, as well as other makeup products such as foundations. Common gel products include anti-acne solutions and skin conditioners. Common liquid form products include anti-acne solutions, perfumes/colognes, aftershaves, gargles/mouthwashes, and toners/bracers/skin conditioners.

Other methodologies and materials for preparing formulations in a variety of forms are also described in Anthony L. L. Hunting (ed.), "A Formulary of Cosmetic Preparations (Vol. 2)-Creams, Lotions and Milks," Micelle Press (England, N.J., 1993). See, for example, Chapter 7, pp. 5–14 (oils and gels); Chapter 8, pp. 15–98 (bases and emulsions); Chapter 9, pp. 101–120 ("all-purpose products"); Chapter 11, pp. 185–208 (foundations, vanishing and day creams); Chapter 12, pp. 209–254 (emollients); Chapter 13, pp. 297–324 (facial treatment products); Chapter 14, pp. 325–380 (hand products): Chapter 15, pp. 381–460 (body and skin creams and lotions); and Chapter 16, pp. 461–484 (baby products); the contents of which are incorporated herein by reference.

The compositions and formulations of the present invention can also be incorporated into other articles for use. For example, the compositions of the invention can be incorporated into bandages to increase wound healing and reduce subject discomfort. Methods of incorporating a ROM production and releasing inhibitory compound into a wound dressing are readily apparent to those of ordinary skill in the art. A discussion of incorporating active materials into a wound dressing is found in U.S. Pat. No. 5,116,620, which is hereby incorporated by reference.

Topical Compound Administration

Administration of the present invention's compounds is often through a topical application. Typical modes of delivery include application using the fingers; application using a physical applicator such as a cloth, tissue, swab, stick or brush; spraying (including mist, aerosol or foam spraying); dropper application; sprinkling; soaking; and gargling or rinsing. Other modes of application include applying the compounds and compositions of the present invention onto a bandage or wound dressing to hold the compounds in communication with a wound site.

Controlled release vehicles can also be used to administer the compounds of the present invention. The technology and products in this art are variably referred to as controlled release, sustained release, prolonged action, depot, repository, delayed action, retarded release and timed release; the words "controlled release" as used herein is intended to incorporate each of the foregoing technologies.

Numerous controlled release vehicles are known, including biodegradable or bioerodable polymers such as polylactic acid, polyglycolic acid, and regenerated collagen. Known controlled release drug delivery devices include creams, lotions, tablets, capsules, gels, microspheres, and liposomes. Transdermal formulations, from which active ingredients are slowly released are also well known and can be used in the present invention.

Controlled release preparations can be achieved by the use of polymers to complex or absorb the histamine. The controlled delivery can be exercised by selecting appropriate macromolecule such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of active compound.

Hydrogels, wherein the histamine compound is dissolved in an aqueous constituent to gradually release over time, can be prepared by copolymerization of hydrophilic monoolefinic monomers such as ethylene glycol methacrylate. Matrix devices, wherein the histamine is dispersed in a matrix of carrier material, can be used. The carrier can be porous, non-porous, solid, semi-solid, permeable or impermeable. Alternatively, a device comprising a central reservoir of histamine surrounded by a rate controlling membrane can be used to control the release of histamine. Rate controlling membranes include ethylene-vinyl acetate copolymer or butylene terephthalate/polytetramethylene ether terephthalate. Use of silicon rubber depots are also contemplated.

Controlled release oral formulations are also well known. Active compound is incorporated into a soluble or erodible matrix. Hydrophilic gums, such as hydroxymethylcellulose, are commonly used. A lubricating agent such as magnesium stearate, stearic acid, or calcium stearate can be used to aid in the tableting process.

In a preferred embodiment, transdermal patches, steady state reservoirs sandwiched between an impervious backing and a membrane face, and transdermal formulations, can also be used to deliver histamine and histamine agonists. Transdermal administration systems are well known in the art. Occlusive transdermal patches for the administration of an active agent to the skin or mucosa are described in U.S. Pat. Nos. 4,573,996, 4,597,961 and 4,839,174, which are hereby incorporated by reference. One type of transdermal patch is a polymer matrix in which the active agent is dissolved in a polymer matrix through which the active ingredient diffuses to the skin. Such transdermal patches are disclosed in U.S. Pat. Nos. 4,839,174, 4,908,213 and 4,943,435, which are hereby incorporated by reference.

Present transdermal patch systems are designed to deliver smaller doses over longer periods of time, up to days and weeks, whereas the present invention would specifically deliver an effective dose of histamine in a range of between about 1 and 60 minutes, depending upon the dose, with a preferred dose being delivered within about 5 minutes. These patches allow rapid and controlled delivery of histamine. The size of these patches are adapted for placement directly over a wart, a lesion, a herpetic wound, or the like. A rate-controlling outer microporous membrane, or micropockets of histamine dispersed throughout a silicone polymer matrix, can be used to control the release rate. Such rate-controlling means are described in U.S. Pat. No. 5,676,969, which is hereby incorporated by reference. In another preferred embodiment, the histamine is released from the patch into the skin of the patient in about 30 minutes or less. In a preferred embodiment, the histamine is released from the patch at a rate of between about 0.025 mg to 0.3 mg per minute for a dose of between about 0.2 mg and 3 mg per patch.

These transdermal patches and formulations can be used with or without use of a penetration enhancer such as dimethylsulfoxide (DMSO), combinations of sucrose fatty acid esters with a sulfoxide or phosphoric oxide, or eugenol. The use of electrolytic transdermal patches is also within the scope of the present invention. Electrolytic transdermal patches are described in U.S. Pat. Nos. 5,474,527, 5,336,168, and 5,328,454, the entire contents of which are hereby incorporated by reference.

In another embodiment transmucosal patches designed for placement over a wound, lesion, or wart can be used to administer the active ingredients of the present invention. An example of such a patch is found in U.S. Pat. No. 5,122,127, which is hereby incorporated by reference. The described patch comprises a housing capable of enclosing a quantity of therapeutic agent where the housing is capable of adhering to mucosal tissues, for example, in the mouth. A drug surface area of the device is present for contacting the mucosal tissues of the host. The device is designed to deliver the drug in proportion to the size of the drug/mucosa interface area. Accordingly, drug delivery rates may be adjusted by altering the size of the contact area.

The housing is preferably constructed of a material that is nontoxic, chemically stable, and non-reactive with the compounds of the present invention. Suitable construction materials include: polyethylene, polyolefins, polyamides, polycarbonates, vinyl polymers, and other similar materials known in the art. The housing can contain means for maintaining the housing positioned against the mucosal membrane. The housing can contain a steady state reservoir positioned to be in fluid contact with mucosal tissue.

Steady state reservoirs for use with the compounds of the present invention will delivery a suitable dose of those compounds over a predetermined period of time. Compositions and methods of manufacturing compositions capable of absorption through the mucosal tissues are taught in U.S. Pat. No. 5,288,497, which is hereby incorporated by reference. One of skill in the art could readily how to include the compounds of the present invention in these and related compositions.

The steady state reservoirs for use with the present invention are composed of compounds known in the art to control the rate of drug release. In one embodiment, the transmucosal patch delivers a dose of histamine over a period of time from about 2 to 60 minutes. The steady state reservoir contained within the housing can carry doses of histamine and other ROM production and release inhibitory compounds in doses from about 0.2 to 5 mg per patch. Transdermal patches that can be worn for several days and that release the compounds of the present invention over that period of time are also contemplated. The reservoirs can also contain permeation or penetration enhancers, as discussed above, to improve the permeability of the active ingredients of the present invention across the mucosal tissue.

Another method to control the release of histamine incorporates the histamine into particles of a polymeric material such as polyesters, polyamino acids, hydrogels, poly lactic acid, or ethylene vinylacetate copolymers.

Alternatively, instead of incorporating histamine into these polymeric particles, histamine is entrapped in microcapsules prepared, for example, by coacervation techniques, or by interfacial polymerization, for example hydroxymethylcellulose or gelatin-microcapsules, respectively, or in colloidal drug delivery systems, for example, liposomes, albumin microspheres, microemulsions, nanoparticles, and nanocapsules, or in macroemulsions. Such technology is well known to those of ordinary skill in pharmaceutical sciences.

In another embodiment, histamine, a $H_2$-receptor agonist, in a total concentration of about 0.0001 to about 0.5 percent by weight of formulation, more preferably about 0.001 to about 0.01 percent by weight of formulation, and most preferably about 0.002 to 0.05 percent by weight of formulation can be administered. ROM scavenging compounds can also be administered in combination with the ROM production and release inhibitory compounds described above.

Administration of each dose of histamine can occur from once a day to up to about twenty times a day, with five times a day being preferred. Additionally, the compounds, compositions and formulations of the present invention can be administered quantum sufficiat, or as much as may be needed to ease the pain or discomfort of the subject. Hourly administrations are also contemplated, however, administrations should not exceed 20 per day.

The administration of the compounds of the present invention can be alone, or in combination with other compounds effective at treating the various medical conditions contemplated by the present invention. For example, histamine can be used to treat a patient suffering from a sunburn in conjunction with other compounds such as aloe vera and or lidocaine to ease subject discomfort. For example, SOOTH-A-CAINE (Sun Pharmaceuticals, Del Ray, Fla. 33447) is just such an aloe vera based product. For an additional example see U.S. Pat. No. 5,558,914, entitled, "Water-based formulation for the treatment of sunburn," hereby incorporated by reference. Further, the compounds of the present invention can be used with a variety of antiviral, antibacterial, or antifungal compounds known and administered by those of skill in the art. Also, the compounds of the present invention, such as histamine, can be administered with a variety of analgesics, anesthetics, or anxiolytics to increase patient comfort during treatment.

Administration of each dose of a compound which induces histamine release can occur from once per day to up to about ten times a day, with five times per day being preferred. Alternatively, administration can be as often as the subject requires to ease wound or skin lesion discomfort. Administration is contemplated as being topical and can incorporate a controlled release mechanism of the type disclosed above. Any controlled release vehicle capable of administering a therapeutically effective amount of a compound that induces the release of endogenous histamine stores can be used.

Administration of ROM production and release inhibitory compounds by injection in conjunction with the topical administration of these compounds is also contemplated. The administration of these compounds is taught in the co-pending application entitled, "Treatment and Prevention of Reactive Oxygen Metabolite-Mediated Cellular Damage," which is hereby incorporated by reference.

The following examples teach the methods of the present invention and the use of the disclosed ROM production and release inhibiting compounds. These examples are illustrative only and are not intended to limit the scope of the present invention. The treatment methods described below can be optimized using empirical techniques well known to those of ordinary skill in the art. Moreover, artisans of ordinary skill would be able to use the teachings described in the following examples to practice the full scope of the present invention.

EXAMPLES

Herpes Infections

The herpesviridae family contains some of the most important human pathogens known. The herpes simplex viruses and varicella-zoster virus are two of these pathogens that cause damage to the skin and mucous membranes. The herpes simplex viruses damage the tissues of the mouth and or throat, eyes, and can infect any dermal or mucosal tissue that has been damaged. For example, herpetic whitlow is a condition that is an infection of the fingers or hands caused by a herpes simplex virus infection. The infection occurs usually by direct inoculation of the virus through broken skin.

Herpes infections are recurrent and extremely painful. The level of discomfort may be attributed to the fact that the herpes virus lies dormant in the trigeminal ganglion of the subject and then pass through the nerves to the skin surface during an outbreak. A brief prodromal period of hyperesthesia typically heralds the development of a cluster of vesicles, generally around the mucocutaneous junction on the lips, in herpes labialis.

EXAMPLE 1

Herpes Labialias

The compounds of the present invention are prepared in a cream for topical application according to procedures well known in the art. The ROM production or release inhibition compound histamine dihydrochloride in a concentration of 0.08% by weight of formulation is added to the cream. Two groups of 10 subjects are selected who are suffering from active herpetic lesions. The first group of 10 subjects suffering from herpetic lesions, the experimental group, is treated with the cream containing histamine dihydrochloride. The second group, the control group, is treated with a control cream that is composed of the same ingredients and compounds of the experimental cream, however, it lacks histamine dihydrochloride.

Treatment of the subjects consists of the topical application of the medication four to five times a day at the lesion site. When treating herpetic vesicles that have not yet ruptured, care is taken to maintain the membrane covering the intact vesicle. When treating herpetic vesicles that have ruptured, care is taken not to contaminate new areas with viral particles.

Subjects in the experimental group experience a decrease in healing time as compared to the control group.

EXAMPLE 2

Treatment of Herpes Labialis in Conjunction with other Therapeutic Herpes Simplex Compounds The ability of the compositions of the present invention to facilitate herpes simplex outbreak treatment using standard compositions is next investigated. The ability of the ROM production and release inhibition compounds of the present invention to increase the effectiveness of 9-(2-Hydroxyethoxymethyl)guanine, ZOVIRAX, (GlaxoWellcome) is evaluated in two groups of 10 subjects each. No subjects are suffering from active lesions at the initiation of the study. Group I subjects receive ZOVIRAX according to the dosage given by the manufacturer. Group II subjects receive ZOVIRAX at the same dose and apply the ROM production and release inhibiting compound histamine dihydrochloride at 0.08% by weight in a cream formulation to the general area at which a herpetic vesicle is thought to be forming when prodromal symptoms appear. Application of the cream continues during vesicle formation and until the vesicles have completely healed. Subjects in both groups are instructed to topically apply the product five times a day at the lesion site. Subjects participating in the study are instructed to monitor the size and duration of the lesions during the herpetic episode. Subjects receiving both the ZOVIRAX and the ROM inhibitory cream show a decrease in the size of the herpetic lesions forming during the outbreak period as compared to the ZOVIRAX alone control group.

EXAMPLE 3

Treatment of Herpes Genitalis using a Foam and a Cream

A female subject suffering from herpes genitalis is treated with the ROM inhibitory compound histamine diphosphate in a concentration of 0.07% by weight of formulation in the form of a foam and a cream. Using an applicator, the foam is injected into the vaginal space to treat herpetic lesions therein. The cream is applied topically to external lesions. The cream and foam are applied three times a day for a period of five days. There are no untoward reactions and the treatment reduced the healing time of the ruptured herpetic vesicles.

EXAMPLE 4

Treatment of Herpes Labialis Using a Cosmetic

A subject suffering from herpes labialis is treated with the ROM inhibitory compound histamine diphosphate in a concentration of 0.07% by weight of formulation in the form of lipstick. The treatment consists of topical application three times a day for a period of five days. There are no untoward reactions and the treatment reduced the healing time of the ruptured herpetic vesicles.

EXAMPLE 5

Treatment of Pharyngotonsillitis

A subject suffering from pharyngotosillitis, a herpetic infection of the pharyngeal region is treated with a mouthwash containing the ROM inhibitory compound NADPH oxidase inhibitor diphenlyeneiodonium in a concentration of 0.05% by weight of formulation. The treatment consists of five mouthwash applications per day for a period of seven days. The administration of diphenlyeneiodonium was effective in treating the pharyngotosillitis of the subject.

EXAMPLE 6

Treatment of Keraconjunctivitis

A subject presenting keratoconjunctivitis or a corneal herpes infection is treated with the compositions of the present invention using an ophthalmic solution of histamine dihydrochloride at 0.09% by weight of formulation. Commercially available ophthalmic solutions are well known in the art. Additionally, the ophthalmic solution contains ZOVIRAX in an effective concentration. Application of the solution to the eye occurs every three hours. A solution containing only the ROM production and release inhibiting compound is given hourly to ease the discomfort of the subject. Application of the solutions reduces the time period of viral activity, the damage caused by the viral outbreak and reduces the discomfort of the patient.

Varicella-Zoster Virus

Varicella (chickenpox) is caused by the varicella-zoster virus (VZV). Like other herpesviruses it is highly infectious. Transmission occurs from person-to-person by direct contact or through the air.

In the absence of vaccination almost everyone develops varicella at some time during his or her life. There were an estimated 4 million cases of varicella in the United States in the early 1990s. There are an estimated 5,000–9,000 hospitalizations each year for varicella and its complications, and in recent years there have been 100 deaths annually with varicella as an underlying cause.

Varicella is characterized by a papulovesicular rash that becomes a noninfectious, dried crust over a five to six day period. Papulovesicular means that both papules (pimple-like eruptions) and vesicles (blister-like eruptions) are present. A person with varicella is contagious from one to two days before the rash appears until all of the eruptions have formed scabs. The disease is usually mild among children. Sometimes a fever or other symptoms precede the rash by a few days. Disease among adults tends to be more severe than that among children and is more likely to result in hospitalization.

Complications from varicella are most likely to occur among people who have compromised immune systems, neonates, and adults. Secondary bacterial infections can result from a varicella infection. Accordingly, it is particularly important to care for the scabbed over eruptions. After infection, the virus remains latent in human nerve tissue and may reactivate, resulting in zoster (shingles).

EXAMPLE 7

Treatment of Varicella-Zoster Virus (Chicken Pox) Infection

A child presenting the symptoms of chicken pox is treated with the compounds of the present invention. In this example, two products are used to treat the subject. The first is a paste containing histamine dihydrochloride at 0.02% by weight of formulation, that is applied to the subject's skin in the areas with vesicle formation. The paste is applied five times per day until the vesicles have completely healed. Additionally, a soap containing histamine dihydrochloride at 0.1% by weight of formulation, is also used during bathing periods to cleanse the areas of skin with vesicles. Application of the cream and periodic cleansing of the vesicles with the soap of the present invention causes the vesicles to heal rapidly and it decreases the level of discomfort experienced by the subject.

EXAMPLE 8

Treatment of Herpes Zoster (Shingles) Lesions

A subject presenting herpes zoster or shingles lesions is treated with the compounds of the present invention in the form of an ointment. The ointment contains an effective concentration of 9-cis-retinoic acid in the amount of approximately 0.003% by weight of formulation. The ointment is administered topically to shingles lesions four times a day until the lesions completely heal.

EXAMPLE 9

Treatment of Herpes Zoster (Shingles) Lesions

A subject presenting herpes zoster or shingles lesions is treated with the compounds of the present invention in the form of a spray. The spray contains an effective concentration of histamine dihydrochloride in the amount of approximately 0.005% by weight of formulation. The spray is administered topically to shingles lesions four times a day until the lesions completely heal.

EXAMPLE 10

Treatment of Herpes Zoster (Shingles) Lesions

A subject presenting herpes zoster or shingles lesions is treated with the compounds of the present invention in the form of an ointment. The ointment contains an effective concentration of histamine dihydrochloride in the amount of approximately 0.004% by weight of formulation. The ointment is administered topically to shingles lesions four times a day until the lesions completely heal. A subcutaneous injection of histamine at a concentration of 10 $\mu$g/kg of the subject is also administered. The injection is given once per week. The administration of these compounds reduces the time required for the healing of the herpetic lesions.

Treatment of Skin Disorders Damaged Skin

The compositions and methods of the present invention contemplate utility in the treatment of a variety of skin disorders including psoriasis, eczema, sunburn, thermoburn, chemical burn, and damage by laceration and various cosmetic surgery techniques.

Psoriasis

Psoriasis is a skin condition characterized by red patches on the skin, topped with a heavy, silvery, sloughing scale. Typically the areas of the body affected are the knees, elbows, scalp, hands and feet. Generally, five percent or less of total body area is affected by the disease. A subject suffering from this condition is in constant discomfort due to the itchy, inflamed, and cracking state of the affected skin.

Furthermore, psychological effects typically result as the subject feels embarrassment over his or her appearance and fear that the disease will become worse.

Presently, treatment for this condition is centered on the temporary relief of symptoms. Typical treatment protocols attempt to keep the skin pliable, and to reduce the inflammation and scaling. Regular applications of creams, ointments and medicated shampoos are necessary. Phototherapy using artificial ultraviolet light type B (UVB) or type A (UVA) in conjunction with psoralen medications, is common. Although a 90% success rate can be obtained with this therapy, up to 30 treatments may be required to attain clearance. Some patients also require continuing treatment or intervals of treatment.

EXAMPLE 11

Treatment of Psoriasis

A subject suffering from psoriasis of the scalp is treated with a shampoo containing approximately 0.008% by weight of histamine dihydrochloride. The subject undergoes UVB treatment in accordance with a protocol well known to those of ordinary skill in the art. In addition, the subject washes her hair once per day with the shampoo containing the ROM production and release inhibitory compound histamine. The shampoo and active ingredient reduces the irritation of the affected area by reducing the ROM concentration of the affected tissues. The subject experiences a reduction in symptoms at a greater rate than a subject receiving UVB treatment alone.

Eczema

Eczema is a common skin disorder. This condition is also known as atopic dermatitis and shares several features with asthma and allergic rhinitis (hay fever). They are all considered allergic illnesses. Eczema can start anytime from infancy to young adulthood.

Almost any part of the skin surface can be involved. When the disease starts in infancy, the rash tends to be localized on the face and scalp. In older individuals, the skin lesions usually occur on the chest, large folds of the extremities, the elbow creases and behind the knees. Although these are the most common sites, other areas can also be affected.

The main problem in eczema is that the skin loses water and dries out causing intense itching. If left alone, the skin would probably show little or no changes (a frequent description of eczema is that it is "the itch that rashes"). The scratching is most severe at night and the skin becomes raw and may begin to ooze. The production of ROMs, as well as TNF-α and IL-1 exacerbate the tissue damage. Eczema appears in cycles, and when the subject is symptom free, the skin becomes thickened and leathery.

EXAMPLE 12

Treatment of Eczema

A subject presenting eczema is treated with a lotion and soap containing the ROM production and release inhibitory compound histamine dihydrochloride. The soap contains histamine in a concentration of approximately 0.1% by weight while the lotion contains histamine in a concentration of approximately 0.0055% by weight. The subject bathes with the soap once daily. The affected area is lathered well with the soap, rinsed, and the procedure is repeated. Following the bath, the lotion is applied up to five times throughout the day to the affected area. The treatment results in a decrease in the symptoms and an increase in the general condition of the skin in the affected area.

EXAMPLE 13

Treatment of Photodermatitis (Second Degree Sunburn)

The ROM production and release inhibitory compound serotonin is used in a gel to treat a subject presenting photodermatitis (second degree sunburn) and attendant blister formation. The subject has blister formation as well as deep reddening of the epidermis on the back. The subject is treated with a gel application such as SOOTH-A-CAINE (Sun Pharmaceuticals, Del Ray, Fla. 33447), which is an aloe vera based product, that also contains an effective dose of histamine in a concentration of 0.006% by weight of formulation. The effect of this administration is a reduction of discomfort in the subject as well as a decrease in blistering and the amount of skin sloughed off as a result of the irradiation.

EXAMPLE 14

Reduction of Photodermatitis Symptoms

A sunscreen formulated according to methods well known in the art is formulated to contain histamine as the ROM production and release inhibitory compound of the present invention. Histamine is present in the sunscreen in a concentration of 0.004% by weight of the formulation.

EXAMPLE 15

Treatment of Thermal Burn Injuries

The compositions of the present invention are administered topically to a subject presenting thermal burn injuries. A water-based gel preparation containing of 0.007% by weight of the formulation of serotonin was administered to the subject's burn injuries. The treatment consisted of topical application of the gel to the burn site every 10 minutes for the first hour, then every 30 minutes for the next three hours. Topical applications thereafter are applied as needed by the subject in response to pain. Application of the gel reduces the discomfort of the subject and promotes healing of the burn injuries.

EXAMPLE 16

Treatment of Chemical Burn Injuries

The compositions of the present invention are administered topically to a subject presenting chemical burn injuries. A water-based gel preparation containing of 0.007% by weight of the formulation of histamine dihydrochloride was administered to the subject's burn injuries. The treatment consisted of topical application of the gel to the burn site every 10 minutes for the first hour, then every 30 minutes for the next three hours. Topical applications thereafter are applied as needed by the subject in response to pain. Application of the gel reduces the discomfort of the subject and promotes healing of the burn injuries.

EXAMPLE 17

Promotion of Incision Healing

The compositions of the present invention are administered topically to a subject presenting an incision of the skin.

A formulation containing histamine dihydrochloride in a concentration of 0.0045% by weight of the formulation, vitamin A at 2000 IU, vitamin E at 5000 IU, and a topical antibiotic is applied to the wound following proper wound cleansing. Subsequent administration of the formulation occurs twice a day and with each change of wound dressing. Application of the formulation promotes healing of the incision and reduces scar formation.

Cosmetic Surgery: Chemical Peels

The technique of chemical peel is used to smooth the texture of the skin of the face by removing its damaged outer layers. It uses a chemical solution, e.g. Phenol, trichloroacetic acid (TCA) and alphahydroxy acids (AHAs). AHAs produce the light peel used for minor cases. TCA is used for medium depth peeling while Phenol is used for deep peeling. Chemical peel can help those individuals with fine to coarse wrinkles, facial blemishes, sun-damaged skin areas, precancerous skin growth, acne and uneven skin pigmentation. Chemical peel can be used alone or in conjunction with a facelift or a forehead lift.

The chemical peel is normally a safe procedure when it is performed by a qualified and experienced plastic surgeon. However, a certain degree of tissue damage occurs during this procedure. ROMs are released into this damaged tissue causing discomfort for the subject as well as lengthening the time required for healing.

EXAMPLE 18

Promotion of Chemical Peel Wound Healing

A subject having undergone the procedure of a chemical peel is treated with a solution containing 0.008% by weight of histamine dihydrochloride to ease the tissue damage caused by the procedure and to promote healing of the treated skin. The solution is applied by soaking the treated five times daily to the treated area. The rate of healing is increased in those area treated with the solution.

Cosmetic Surgery: Laser Treatment

One method of resurfacing the skin is to apply laser light energy to the skin. This treatment can remove, for example, fine facial wrinkling, deep laugh and frown lines, chicken pox scars, acne scars, irregular surgical or traumatic scars and superficial pigmented lesions. During the treatment, which commonly employs a $CO_2$ laser, the light energy is used to vaporize the top layer of skin, or epidermis.

The elimination of this tissue causes the contraction of the papillary dermis, or second skin layer. For the first 48 to 72 hours after surgery, the face is bright red, sore, oozing and itchy. Some people have less reaction than others. The skin grows back in about a week. In two weeks, swelling is mostly down and the redness often can be toned down with cosmetics. It may take six weeks to six months for all of the redness to go away. It is especially important to use sunscreen liberally after the procedure.

The combined effect creates a smoother, tighter skin surface. This treatment also results in the release of ROMs and secondary cytokines that can unnecessarily increase the amount of tissue damage in the treated area as well as prolong the time of healing.

EXAMPLE 19

Promotion of Laser Skin Resurfacing Wound Healing

A subject having undergone the procedure of a laser facial resurfacing is treated with a bandage treated with a sterile solution containing 0.008% by weight of histamine dihydrochloride to ease the tissue damage caused by the procedure and to promote healing of the treated skin. The bandage containing the sterile solution of histamine dihydrochloride is applied five times daily to the treated area. A sunscreen containing 0.008% by weight of histamine dihydrochloride is also applied before the subject is to be exposed to sunlight. The treatment continues until the skin in the treated area has completely regrown. The rate of healing is increased in those area treated with the solution.

Periodontal Disease

Periodontal disease is an infection of the tissues surrounding and supporting the teeth. It is a major cause of tooth loss in adults. In fact, after age 35, some form of gum disease affects about three out of four adults.

Periodontal disease is caused by plaque, a sticky film of bacteria that constantly forms on the teeth. These bacteria create toxins that can damage the gums. Furthermore, this chronic bacterial infection results in the generation of ROMs and secondary cytokines that inadvertently assist the bacterial toxins in damaging the gum tissue. In the early stage of gum disease, called gingivitis, the gums can become red, swollen and bleed easily. At this stage, the disease is still reversible and can usually be eliminated by daily brushing and flossing.

Because gum disease is usually painless, however, it often goes undetected. In the more advanced stages of gum disease, called periodontitis, the gums and bone that support the teeth can become seriously damaged. The teeth can become loose, fall out or have to be removed by a dentist. Symptoms of periodontal disease include: gums that bleed when the teeth are brushed; red, swollen or tender gums; gums that have pulled away from the teeth; bad breath that doesn't go away; pus between the teeth and gums; loose teeth; a change in the way the teeth fit together when biting; a change in the fit of partial dentures.

EXAMPLE 20

Treatment of Periodontal Disease

A subject presenting periodontal disease is treated with a mouthwash and toothpaste, each containing 0.008% by weight of histamine dihydrochloride. The subject brushes her teeth three times daily with the toothpaste for ten minutes. Following this cleansing, the subject washes her mouth with the mouthwash, rinses with water, and repeats. The treatment continues until the health of the periodontal tissue improves. The rate of healing is increased when the affected area is treated with the combination of mouthwash and toothpaste.

Conclusion

We have discovered that the topical application of ROM production and release inhibitory compounds can promote healing and reduce the discomfort of a variety of skin conditions. The detrimental effects of unwanted ROMs are removed when the compounds of the present invention are topically applied. Further, scavengers of ROMs can assist in reducing the negative effects of unwanted ROM production.

Finally, the forgoing examples are not intended to limit the scope of the present invention, which is set forth in the following claims. In particular, various equivalents and substitutions will be recognized by those of ordinary skill in the art in view of the foregoing disclosure, and these are contemplated to be within the scope of the present invention.

What is claimed is:

1. A cosmetic composition comprising an effective dose of a compound that inhibits the enzymatic production or release of ROMs in a cosmetically acceptable carrier adapted for topical delivery as a cosmetic product, said carrier is selected from the group consisting of a makeup product, a hair care product, an underarm deodorant product, a perfume, a cologne, an aftershave, and a lotion.

2. The composition of claim 1, wherein said compound is selected from the group consisting of histamine, histamine dihydrochloride, histamine diphosphate, other histamine salts, esters, prodrugs, $H_2$ receptor agonists, serotonin, and 5HT agonists.

3. The composition of claim 1, wherein said compound is a compound that promotes the release of endogenous histamine stores.

4. The composition of claim 3, wherein said compound that promotes the release of endogenous histamine stores is selected from the group consisting of IL-3, retinoic acid, 9-cis-retinoic acid, all-trans-retinoic acid, and allergens.

5. The composition of claim 1, wherein the makeup product is selected from the group consisting of a foundation, a blush, and a lipstick.

6. The composition of claim 1, wherein the hair care product is selected from the group consisting of a hair dye, a shampoo, and a conditioner.

7. The composition of claim 1, wherein the cosmetically acceptable carrier further comprises a colorant.

8. The composition of claim 7, wherein the colorant is selected from the group consisting of FD&C Red No. 40 and FD&C Yellow No. 5.

9. The composition of claim 1, wherein the cosmetically acceptable carrier further comprises a fragrance.

* * * * *